(12) United States Patent
Fernandes et al.

(10) Patent No.: US 9,858,792 B2
(45) Date of Patent: Jan. 2, 2018

(54) SMART SWIMMING POOL OR HOT TUB MONITOR

(71) Applicant: CEC—Comunicações e Computadores SA, Trajouce (PT)

(72) Inventors: Antonio Pedro Fernandes, Lisbon (PT); Carlos Formigal Silva, Lisbon (PT); Francis Spruit, Hercules, CA (US); Maria Ana Cunha, Parede (PT); Margarida Cabral Noeme, Oeiras (PT); Catarina Saraiva Fernandes, Caxias (PT); Ana Cristina Moreira, Alcabideche (PT); Daniel Cabral Fidalgo, S. João das Lampas (PT); Pedro Homem Ferreria, Olival Basto (PT); Margarida Manuel Henriques, Ericeira (PT)

(73) Assignee: CEC, SA, Sao Domingo de Rana (PT)

( * ) Notice: Subject to any disclaimer, the term of this patent is extended or adjusted under 35 U.S.C. 154(b) by 0 days.

(21) Appl. No.: 15/279,111

(22) Filed: Sep. 28, 2016

(65) Prior Publication Data

US 2017/0092096 A1    Mar. 30, 2017

Related U.S. Application Data

(60) Provisional application No. 62/233,973, filed on Sep. 28, 2015.

(51) Int. Cl.
| | | |
|---|---|---|
| G08B 19/00 | (2006.01) | |
| G08B 21/08 | (2006.01) | |
| E04H 4/00 | (2006.01) | |
| H04L 29/08 | (2006.01) | |

(52) U.S. Cl.
CPC ............ *G08B 21/084* (2013.01); *E04H 4/00* (2013.01); *H04L 67/12* (2013.01)

(58) Field of Classification Search
CPC ......... G08B 19/00; G08B 21/00; G08B 21/02
USPC ....................................... 340/539.22, 539.26
See application file for complete search history.

(56) References Cited

U.S. PATENT DOCUMENTS

| | | | | |
|---|---|---|---|---|
| 7,681,436 B2 * | 3/2010 | Biberger | ................ | G01N 33/18 |
| | | | | 210/85 |
| 2016/0042629 A1 * | 2/2016 | Snyder | .................. | G08B 21/08 |
| | | | | 340/573.6 |
| 2016/0266577 A1 * | 9/2016 | Kerzner | ............... | G05D 1/0022 |

* cited by examiner

*Primary Examiner* — Kevin Kim
(74) *Attorney, Agent, or Firm* — Michael L. Greenberg, Esq.; Greenberg & Lieberman, LLC

(57) ABSTRACT

A smart pool maintenance monitor and alert system configured to communicate with an internet-connected device is described. The system employs a floating buoy for use within the water of a swimming pool or hot tub, and a gateway. The buoy is equipped with a variety of environmental sensors configured to accurately and expediently measure water temperature, pH, salinity, water level, air temperature, UV index, the ORP index of the water, and other environmental data. The data is conveyed via a wireless radio to the gateway, which interprets the data, stores the data in cloud storage, and relays it to a user's mobile device where it will be displayed by the applications downloaded to the respective user devices (smartphones, tablets, laptops and PCs, as well TV Set Top Boxes and wearable devices). The gateway is configured to convey alerts to the user when measurements are not consistent with those of a safe and hygienic pool.

10 Claims, 3 Drawing Sheets

US 9,858,792 B2

SMART SWIMMING POOL OR HOT TUB MONITOR

CONTINUITY

This application is a non-provisional application of provisional patent application No. 62/233,973, filed on Sep. 28, 2015, and priority is claimed thereto.

FIELD OF THE PRESENT INVENTION

The present invention relates generally to pool monitoring hardware, and more specifically relates to an internet-connected water-testing device, configured to provide easy and expedient access to water quality monitoring features of a pool or hot tub from any location via a smartphone or other internet-connected device. Also, the present invention incorporates weather station functionality that provides the user weather data specific to the user's residence and pool environment from any location via a smartphone or other internet-connected device.

BACKGROUND OF THE PRESENT INVENTION

A swimming pool and/or hot tub is often at the forefront of many dream homes of Americans, and are popular in countless homes and communities all over the world. They provide cool and relaxing places for individuals to de-stress and unwind, and are a delight in the summertime. Unfortunately, much to the dismay of many pool owners, pool maintenance is not usually a fun task. Keeping a swimming pool or hot tub requires weekly (occasionally biweekly) water testing, pump and filter maintenance, water skimming, chemical mixing, and adding acids, chlorine and other chemicals to the water. Without maintenance such as this, pools can quickly become unsanitary and even unsafe for swimmers. Algae build up can quickly overtake a pool in warm climates, causing the owner to 'shock' and clean the pool over a period of time. This often requires timely addition of chemicals, which can easily be forgotten. Without consistent maintenance, pools can quickly become unusable. To some, the maintenance is cumbersome and droll, and therefore, the pool can become neglected, and the maintenance duty schedule forgotten.

Even more, there is a need for a convenient and more accurate pool or hot tub monitor than is currently on the market. For example, unless various readings can be interpolated to give an overall picture of that which is taking place in a pool or hot tub, the single readings alone might not trip an alert that something is awry in a pool or hot tub. In other words, there is a need for a pool or hot tub monitor that can piece readings together to alert when a few readings might not cause alarm if they are not correlated together.

Thus, there is a need for a smart pool maintenance device and system configured to interface with the mobile, or other internet-connected devices of the user, and alert him or her with real-time data relating to the overall quality of the water and proximal environmental conditions. Such a device would preferably have a buoy component configured to float in the swimming pool water, and a gateway component. The buoy is equipped with sensors to attain pool environmental data, and convey the data wirelessly via wireless radio technology, to the gateway unit. The data is stored on cloud-based servers in communication with the internet, providing for easy access to the data from any internet enabled device. Such a device will promote and safeguard the healthy and safe use of swimming pools and spas.

SUMMARY OF THE PRESENT INVENTION

The swimming pool is a complex environment that requires constant care in order to be used safely, healthily, at a reduced cost and with minimal impact to the environment. The present invention implements all the main activities required to empower the pool owner with knowledge and timely information for maintaining a fun and relaxing pool environment. The present invention provides real time measurement data of key water quality parameters as well as other environmental parameters that affect the water quality and pool experience. Additionally, it measures other parameters that might be harmful for the pool user.

A buoy collects and conveys information to a gateway unit that, by using intelligent algorithms, is capable of informing pool users and technicians about pool conditions in real time. By further combining data from a multitude of swimming pools in nearby regions, a set of algorithms improves the recommendations for better achieving water chemistry balance.

The present invention is a wireless pool monitoring and water-testing device housed within a floating buoy, and a wireless, internet-enabled gateway. The present invention employs two MCUs (Micro Controller Unit, one in the buoy and one in the gateway), one radio unit in the buoy and another one in the gateway as well as one Wi-Fi module and several measurement modules. The present invention employs cloud storage as a means to store measurement data and pool history over time. The present invention is configured to communicate via the gateway to an access point for internet connectivity. The radio module of the present invention ensures the communication of data from the buoy to the gateway and vice-versa. The gateway transmits the measurements (quantitative data) performed by the present invention to the cloud storage. The gateway can also charge the buoy device of the present invention, as well as other devices compatible with the induction-charging platform employed by (and provided via) the gateway of the present invention. It should be understood that the present invention can obtain several measurements, and then obtain a correlation to recommend whether a pool is safe and/or comfortable for use.

The two primary functions of the present invention; water quality monitoring & weather station functionality combined in a single system provides the user all necessary water and environmental data to assist in maintaining a healthy and safe pool and home environment.

BRIEF DESCRIPTION OF THE DRAWINGS

The present invention will be better understood with reference to the appended drawing sheets, wherein.

DETAILED DESCRIPTION OF THE PREFERRED EMBODIMENT

Figure 1:
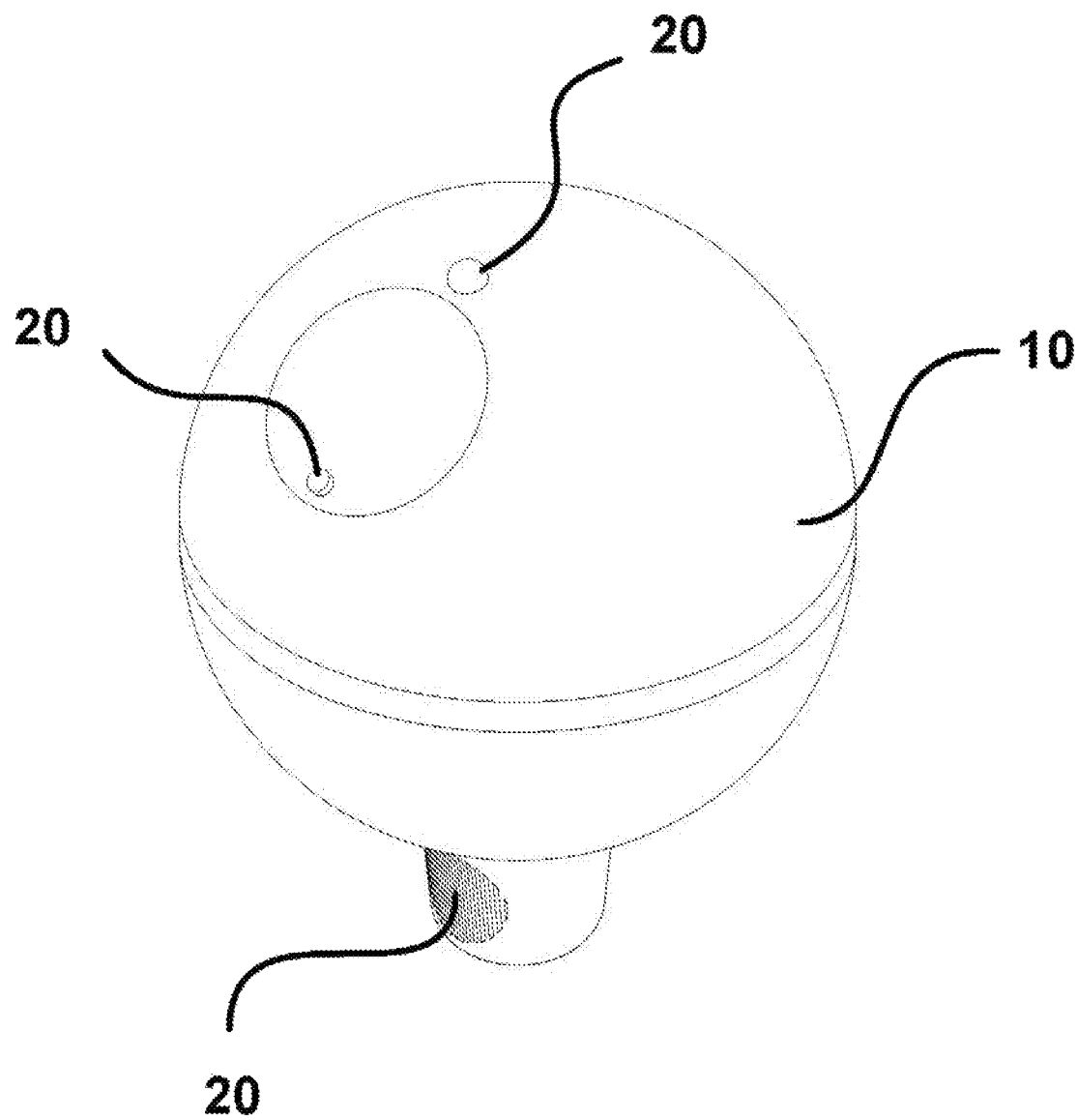
FIG. 1 is a perspective view of the side of the buoy of the present invention.

The present invention is a swimming pool monitoring and management system that employs a buoy (10) and a gateway (40). The buoy (10) is in communication with the gateway (40) via a wireless radio connection established via a high performance low power radio on board the buoy (10) and the gateway (40). The buoy (10) is equipped with a sensor array (20) that is configured to accurately detect and quantitatively measure the conditions of the environment. The sensor array (20) is preferably equipped with at least one temperature sensor, a PH reader, an ORP reader, and an impact detector (conveyed via at least one accelerometer).

The measurements performed by the various sensors of the sensor array (20) of the buoy (10) device of the present invention in the pool are chosen from the following group:

Water Temperature
Air Temperature
UV Index (Ultraviolet)
ORP Index of the Water (Oxygen Reduction Potential)
pH of the Water
3-Axis Accelerometer
Ultra-Sonic Meter
Water level of the pool
Dissolved Oxygen in the Water
Turbidity Meter
Nitrate Index
Air Quality The buoy of the present invention is also configured to perform the following system monitoring measurements:

Battery Voltage Level
System Temperature
Syeceiving Signal Strength Indication (RSSI)

The measurements performed by the various sensors of the gateway (gateway sensors (60)) are chosen from the following group:

Indoor Air Temperature
Indoor Air Quality
Atmospheric Pressure
Humidity

The gateway (40) is configured to receive all data measured by the buoy (10), and will transmit the data to cloud storage services and to mobile platforms. The gateway (40) is configured with an induction charging mechanism (30) configured to be used to charge the buoy device when the battery level of the buoy (10) goes below a certain threshold.

The gateway (40) also houses the alarm speaker that is triggered to sound when the pool is armed for security, and a person or a large object falls into the pool. The present invention, when armed, detects the presence of a large object or person falling into the pool, via an algorithm that analyzes, in the time and frequency domain, the data collected by the accelerometer and ultrasonic sensors disposed within the sensor array (20) of the buoy (10).

The gateway (40) can also monitor the environment inside in the house, where the gateway (40) is preferably located. The gateway (40) of the present invention also acts as a hub for other devices that can be integrated in the system of the present invention.

Figure 2:
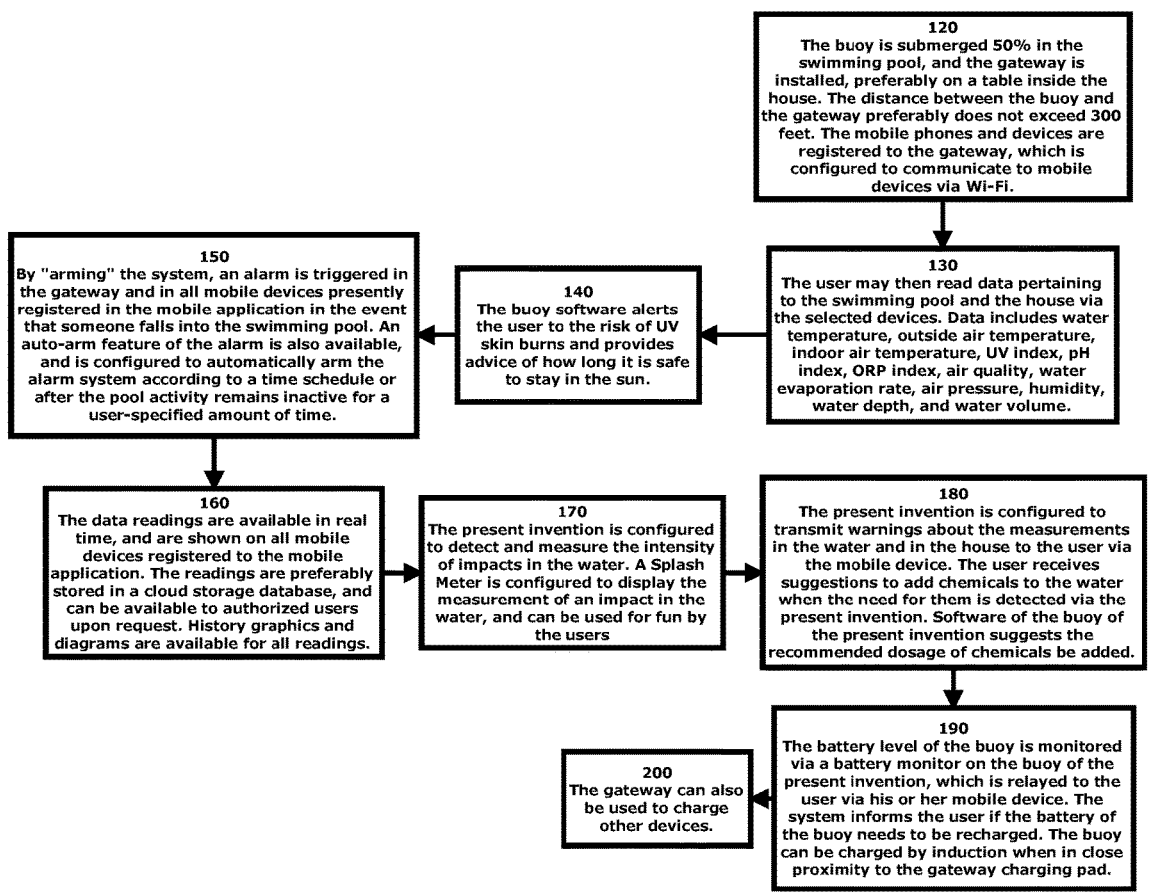
FIG. 2 is a flow chart of the preferred use of the present invention.
Figure 3:
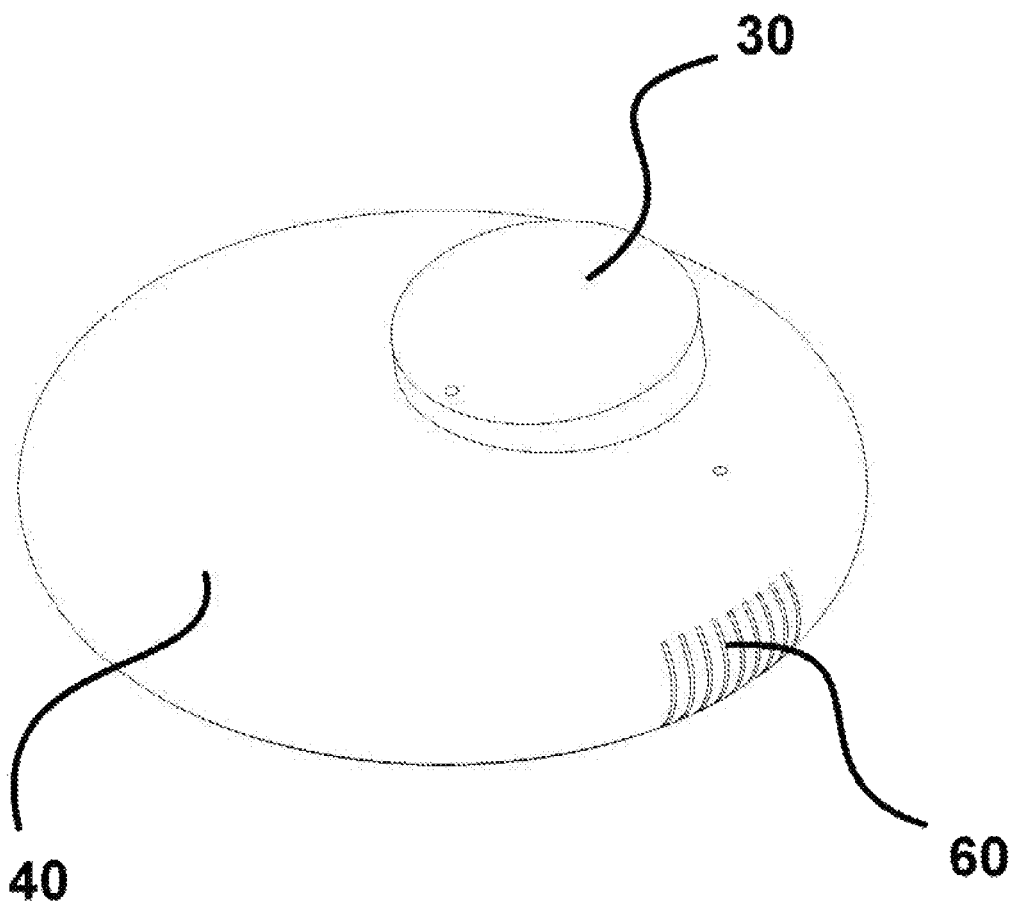
FIG. 3 is a perspective view of the gateway of the present invention.

The process of use of the present invention, as depicted in FIG. 2, is preferably as follows:

1. The buoy (10) is submerged 50% in the swimming pool, and the gateway (40) is installed, preferably on a table inside the house. The distance between the buoy (10) and the gateway (40) preferably does not exceed 300 feet. The mobile phones and devices are registered to the gateway (40), which is configured to communicate to mobile devices via Wi-Fi. The physical dimensions of the swimming pool and other relevant data is provided by the user to the system. (120)

2. All system set-up, configuration and monitoring will take place through device applications which the user will download to those devices which the user intends to use. Smartphones, tablets, laptops, and PCs, as well as TV Set Top Box and wearable device applications are preferably configured to work with the present invention.

3. The user may then read data pertaining to the swimming pool and the house via the selected devices. Data includes water temperature, outside air temperature, indoor air temperature, UV index, pH index, ORP index, air quality, water evaporation rate, air pressure, humidity, water depth, and water volume. (130)

4. The buoy software alerts the user to the risk of UV skin burns and provides advice of how long it is safe to stay in the sun. (140)

5. By "arming" the system, an alarm is triggered in the gateway (40) and in all mobile devices presently registered in the mobile application in the event that someone falls into the swimming pool. An auto-arm feature of the alarm is also available, and is configured to automatically arm the alarm system according to a time schedule or after the pool activity remains inactive for a user-specified amount of time. (150)

6. The data readings are available in real time, and are shown on all mobile devices registered to the mobile application. The readings are preferably stored in a cloud storage database, and can be available to authorized users upon request. History graphics and diagrams are available for all readings. (160)

7. The present invention is configured to detect impacts in the water. When the accelerometer in the buoy measures motion that surpasses a configured threshold an audible alarm will sound in the gateway and an alert notification will be sent to the user's configured devices (smartphones, tablets, laptops, and PCs, as well as TV Set Top Boxes and wearable devices).

8. The present invention is configured to detect and measure the intensity of impacts in the water. A Splash Meter is configured to display the measurement of an impact in the water, and can be used for fun by the users. (170) It is important to note that the Splash Meter provides added incentive to keep the present invention in a pool—even during active pool use. Not only does the buoy (10) of the present invention have a spherical shape, so as not injure a swimmer coming into contact with it (it does not have any pointed surfaces or oblong extensions), but the present invention floats around a pool similar to an unobtrusive ball. Further, as a splash meter, users do not view the present invention as a pool cleaner-type device that should be removed from the pool during use, but users actually want to keep the present invention in the pool during use so that the present invention can measure the amount of splash that occurs as users jump or dive into the pool. Thus, maintaining the present invention in the pool during use is accomplished, and active measurements during pool use allow the present invention to safeguard pool users for hours—as opposed to other pool monitors that users might remove during use.

9. The present invention is configured to transmit warnings about the measurements in the water and in the house to the user via the mobile device. The user receives suggestions to add chemicals to the water when the need for them is detected via the present invention. Software of the buoy of the present invention suggests the recommended dosage of chemicals be added. (180)

10. The battery level of the buoy (10) is monitored via a battery monitor on the buoy (10) of the present invention, which is relayed to the user via his or her mobile device. The system informs the user if the battery of the buoy (10) needs to be recharged. The buoy (10) can be charged by induction when in close proximity to the gateway charging pad (30). (190)

11. The gateway (40) can also be used to charge other devices. (200)

Alternate embodiments of the present invention include variations on the gateway (40), which may be configured to interface with other devices. Therefore, the present invention also allows the integration of other devices via the gateway (40). It is envisioned that the software of the gateway (40) allows for the control of other devices related to home automation. As possible examples, is envisioned that the gateway (40) of the present invention may remotely control the pool pumps, the water heating unit, communicate with outdoor weather stations, and to other alarms systems. The hardware design of the gateway (40) of the present invention allows for the integration of additional sensors, probes and controllers, each of which are preferably disposed outside the buoy (10). The integration of these peripherals is done by wireless connectivity with the gateway (40).

The present invention manages to integrate in the same compact package all the key sensors to get a very detailed picture of the pool environment. By placing all the sensors (sensor array (20)) in the buoy (10), the present invention is capable of informing the pool user about the exact conditions that will be experienced at the pool. By using a combination of the measurements made by the sensor array (20) of the buoy (10) with accelerometer data, and UV/light, the system is able to intelligently weigh, modify and discard all but the relevant data. The gateway (40) utilizes temperature and humidity measurements to compensate the air quality measurements. For accuracy, the gateway (40) is designed with two generous air intake vents, and the PCB (Processor Control Board) has been adjusted to place possible interfering sources away from the sensor array (20). The gateway (40) also uses an intelligent algorithm to compensate temperature skewing during wireless charging activities.

It should be understood that the gateway (40) preferably acts as the system brain, remotely instructing the buoy (10) to perform measurements at the correct time so that it can preserve its battery life. It is crucial that the battery longevity is such that the user does not get bothered constantly to recharge it.

It is envisioned that the buoy (10) will preferably be equipped with an add-on propulsion system to enable the buoy (10) to be used for enhanced fun activities, to automatically perform measurements along several pool locations, and to engage in basic cleaning functionalities. The control of the propulsion system can be either executed manually through the software installed on mobile devices in communication with the buoy (10), or automatically through the algorithms implemented in the gateway (40).

The buoy (10) is preferably equipped with an integrated speaker that is used for basic communication with the user during setup and troubleshooting activities. Additionally, the buoy (10) is equipped with an LED light to complement the previous functions.

The user will be notified when the battery of the buoy (10) runs below a given threshold, and also if the communication with the buoy (10) is interrupted.

The gateway (40) is preferably also equipped with an LED that indicates the correct operation of the system of the present invention. In case of any abnormal event, the LED will flash to warn the user. In parallel, all the detailed information about system malfunctions is conveyed to the mobile devices in communication with the system of the present invention.

In some embodiments of the present invention, the buoy (10) can be upgraded to be charged through a solar panel attachment, coupled together with the propulsion system which can also be used to dispense chemicals throughout the pool.

Having illustrated the present invention, it should be understood that various adjustments and versions might be implemented without venturing away from the essence of the present invention. Further, it should be understood that the present invention is not solely limited to the invention as described in the embodiments above, but further comprises any and all embodiments within the scope of this application.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The exemplary embodiment was chosen and described in order to best explain the principles of the present invention and its practical application, to thereby enable others skilled in the art to best utilize the present invention and various embodiments with various modifications as are suited to the particular use contemplated.

We claim:
1. A pool status and alert system comprising:
a buoy, said buoy disposed within the pool;
a gateway, said gateway in wireless communication with said buoy;
a sensor array, said sensor array disposed within said buoy;
wherein said gateway is in communication with at least one mobile device via the internet;
wherein said sensor array is equipped with the following sensors:
a first thermometer configured to detect the temperature of the water, a second thermometer configured to detect the temperature of the air, an air quality sensor, a three-axis accelerometer, a pH meter, a UV index sensor, an Oxygen reduction Potential index sensor, a nitrate index sensor, a water depth sensor, a hygrometer, an ultrasonic sensor, and a turbidity meter;
wherein said sensor array is configured to obtain quantitative data pertaining to environmental conditions of the pool;
wherein said quantitative data is relayed to said gateway and said at least one mobile device wirelessly;
at least one rechargeable battery, said at least one rechargeable battery disposed within said buoy;
wherein said at least one rechargeable battery powers said sensor array;
wherein said at least one rechargeable battery is configured to be charged via induction; and
wherein said gateway charges said at least one rechargeable battery.

2. A pool status and alert system comprising:
a buoy, said buoy disposed within the pool;
a gateway, said gateway in wireless communication with said buoy;
a sensor array, said sensor array disposed within said buoy;
wherein said gateway is in communication with at least one mobile device via the internet;
wherein said sensor array is equipped with the following sensors:
a first thermometer configured to detect the temperature of the water, a second thermometer configured to detect the temperature of the air, an air quality sensor, a three-axis accelerometer, a pH meter, a UV index sensor, an Oxygen reduction Potential index sensor, a nitrate index sensor, a water depth sensor, a hygrometer, an ultrasonic sensor, and a turbidity meter;
wherein said sensor array is configured to obtain quantitative data pertaining to environmental conditions of the pool;
wherein said quantitative data is relayed to said gateway and said at least one mobile device wirelessly;
gateway sensors, said gateway sensors disposed within said gateway;
wherein said gateway sensors are configured to obtain and record the following measurements as quantitative data:
indoor air temperature, indoor air quality, atmospheric pressure, indoor humidity;
wherein said gateway is housed within a structure adjacent to the pool;
wherein said quantitative data is stored to cloud storage; and
at least one wireless radio, said at least one wireless radio configured to relay said quantitative data to said at least one mobile device via cloud storage.

3. A pool status and alert system comprising:
a buoy, said buoy disposed within the pool;
a gateway, said gateway in wireless communication with said buoy;
a sensor array, said sensor array disposed within said buoy;
wherein said gateway is in communication with at least one mobile device via the internet;
wherein said sensor array is equipped with the following sensors:
a first thermometer configured to detect the temperature of the water, a second thermometer configured to detect the temperature of the air, an air quality sensor, a three-axis accelerometer, a pH meter, a UV index sensor, an Oxygen reduction Potential index sensor, a nitrate index sensor, a water depth sensor, a hygrometer, an ultrasonic sensor, and a turbidity meter;
wherein said sensor array is configured to obtain quantitative data pertaining to environmental conditions of the pool;
wherein said quantitative data is relayed to said gateway and said at least one mobile device wirelessly;
a splash meter, said splash meter generating splash size data on splashes occurring in the pool via said 3-axis accelerometer; and
wherein said splash size data is conveyed wirelessly to said gateway and to said at least one mobile device.

4. The system of claim 1, further comprising:
at least one rechargeable battery, said at least one rechargeable battery disposed within said buoy;
wherein said at least one rechargeable battery powers said sensor array;
wherein said at least one rechargeable battery is configured to be charged via induction;
wherein said gateway charges said at least one rechargeable battery;
a processor control board, said processor control board housed within said buoy, in communication with said rechargeable battery;
wherein said processor control board is isolated from said sensor array, preventing interference;
at least one air vent, said at least one air vent disposed at a top of said gateway; and
wherein said at least one air vent facilitates the generation of said quantitative data pertaining to the air, gathered via said sensor array.

5. A pool status and alert system comprising:
a buoy, said buoy disposed within the pool;
a gateway, said gateway in wireless communication with said buoy;
a sensor array, said sensor array disposed within said buoy;
wherein said gateway is in communication with at least one mobile device via the internet;
wherein said sensor array is equipped with the following sensors:
a first thermometer configured to detect the temperature of the water, a second thermometer configured to detect the temperature of the air, an air quality sensor, a three-axis accelerometer, a pH meter, a UV index sensor, an Oxygen reduction Potential index sensor, a nitrate index sensor, a water depth sensor, a hygrometer, an ultrasonic sensor, and a turbidity meter;
wherein said sensor array is configured to obtain quantitative data pertaining to environmental conditions of the pool;
wherein said quantitative data is relayed to said gateway and said at least one mobile device wirelessly;
a speaker, said speaker disposed within said gateway;
wherein said speaker is configured to sound an alarm when armed for security and triggered via said quantitative data from said 3-axis accelerometer indicates an unexpected body has fallen into the pool;
at least one rechargeable battery, said at least one rechargeable battery disposed within said buoy;
wherein said at least one rechargeable battery powers said sensor array;
wherein said at least one rechargeable battery is configured to be charged via induction; and
wherein said gateway charges said at least one rechargeable battery.

6. A pool status and alert system comprising:
a buoy, said buoy disposed within the pool;
a gateway, said gateway in wireless communication with said buoy;
a sensor array, said sensor array disposed within said buoy;
wherein said gateway is in communication with at least one mobile device via the internet;
wherein said sensor array is equipped with the following sensors:
a first thermometer configured to detect the temperature of the water, a second thermometer configured to detect the temperature of the air, an air quality sensor, a three-axis accelerometer, a pH meter, a UV index sensor, an Oxygen reduction Potential index sensor, a nitrate index sensor, a water depth sensor, a hygrometer, an ultrasonic sensor, and a turbidity meter;

wherein said sensor array is configured to obtain quantitative data pertaining to environmental conditions of the pool;

wherein said quantitative data is relayed to said gateway and said at least one mobile device wirelessly;

a speaker, said speaker disposed within said gateway;

wherein said speaker is configured to sound an alarm when armed for security and triggered via said quantitative data from said 3-axis accelerometer indicates an unexpected body has fallen into the pool;

gateway sensors, said gateway sensors disposed within said gateway;

wherein said gateway sensors are configured to obtain and record the following measurements:

indoor air temperature, indoor air quality, atmospheric pressure, indoor humidity;

wherein said gateway is housed within a structure adjacent to the pool;

wherein said quantitative data is stored to cloud storage; and at least one wireless radio, said at least one wireless radio configured to relay said quantitative data to said at least one mobile device via cloud storage.

7. A pool status and alert system comprising:

a buoy, said buoy disposed within the pool;

a gateway, said gateway in wireless communication with said buoy;

a sensor array, said sensor array disposed within said buoy;

wherein said gateway is in communication with at least one mobile device via the internet;

wherein said sensor array is equipped with the following sensors:

a first thermometer configured to detect the temperature of the water, a second thermometer configured to detect the temperature of the air, an air quality sensor, a three-axis accelerometer, a pH meter, a UV index sensor, an Oxygen reduction Potential index sensor, a nitrate index sensor, a water depth sensor, a hygrometer, an ultrasonic sensor, and a turbidity meter;

wherein said sensor array is configured to obtain quantitative data pertaining to environmental conditions of the pool;

wherein said quantitative data is relayed to said gateway and said at least one mobile device wirelessly;

a speaker, said speaker disposed within said gateway;

wherein said speaker is configured to sound an alarm when armed for security and triggered via said quantitative data from said 3-axis accelerometer indicates an unexpected body has fallen into the pool;

a splash meter, said splash meter generating splash size data on splashes occurring in the pool via said 3-axis accelerometer; and wherein said splash size data is conveyed wirelessly to said gateway and to said at least one mobile device.

8. The system of claim 1, further comprising:

gateway sensors, said gateway sensors disposed within said gateway;

wherein said gateway sensors are configured to obtain and record the following measurements:

indoor air temperature, indoor air quality, atmospheric pressure, indoor humidity;

wherein said gateway is housed within a structure adjacent to the pool;

wherein said quantitative data is stored to cloud storage; and at least one wireless radio, said at least one wireless radio configured to relay said quantitative data to said at least one mobile device via cloud storage.

9. The system of claim 1, further comprising:

a splash meter, said splash meter generating splash size data on splashes occurring in the pool via said 3-axis accelerometer;

wherein said splash size data is conveyed wirelessly to said gateway and to said at least one mobile device; and wherein said buoy is round.

10. The system of claim 2, further comprising:

at least one rechargeable battery, said at least one rechargeable battery disposed within said buoy;

wherein said at least one rechargeable battery powers said sensor array;

wherein said at least one rechargeable battery is configured to be charged via induction;

wherein said gateway charges said at least one rechargeable battery;

a splash meter, said splash meter generating splash size data on splashes occurring in the pool via said 3-axis accelerometer; and wherein said splash size data is conveyed wirelessly to said gateway and to said at least one mobile device.

* * * * *